United States Patent
Chang et al.

(10) Patent No.: US 7,115,865 B2
(45) Date of Patent: Oct. 3, 2006

(54) METHOD OF APPLYING MICRO-PROTECTION IN DEFECT ANALYSIS

(75) Inventors: Ching-Pin Chang, Taipei (TW);
Ching-Ching Shih, Hsin-Chu (TW);
Ting-Wei Chen, Taipei Hsien (TW)

(73) Assignee: Powerchip Semiconductor Corp., Hsin-Chu (TW)

( * ) Notice: Subject to any disclaimer, the term of this patent is extended or adjusted under 35 U.S.C. 154(b) by 0 days.

(21) Appl. No.: 10/908,953

(22) Filed: Jun. 1, 2005

(65) Prior Publication Data

US 2006/0138323 A1    Jun. 29, 2006

(30) Foreign Application Priority Data

Dec. 23, 2004    (TW) .............................. 93140357 A

(51) Int. Cl.
*H01J 37/256*    (2006.01)

(52) U.S. Cl. ...................................... 250/307; 250/309

(58) Field of Classification Search ................ 250/307, 250/309, 311, 492.2, 492.21, 306, 310; 438/700; 216/84, 85, 37, 59

See application file for complete search history.

(56) References Cited

U.S. PATENT DOCUMENTS 6,723,650 B1 *    4/2004    Chang ........................ 438/700

* cited by examiner

*Primary Examiner*—Kiet T. Nguyen
(74) *Attorney, Agent, or Firm*—Winston Hsu

(57) ABSTRACT

The present invention discloses a method of applying micro-protection in defect analysis. The method includes providing a substrate having at least one defect thereon, forming the micro-protection on the surface of the defect, confirming the site of the defect, and forming a specimen of the defect by utilizing a focused ion beam microscope.

19 Claims, 12 Drawing Sheets

METHOD OF APPLYING MICRO-PROTECTION IN DEFECT ANALYSIS

BACKGROUND OF INVENTION

1. Field of the Invention

The present invention relates to a defect analysis method, and more particularly, to a defect analysis method of utilizing at least one nondestructive micro-protection for semiconductor dies or other substrates.

2. Description of the Prior Art

In the semiconductor fabricating process, some small particles and defects are unavoidable. As the size of devices shrinks and the integration of circuits increases gradually, those small particles or defects affect the property of the integrated circuits more seriously. In order to improve the reliability of semiconductor devices, a plurality of tests and monitors is performed continuously to find the root cause of the defects or particles. Then, process parameters can be tuned correspondingly to reduce a presence of defects or particles so as to improve the yield and reliability of the semiconductor fabricating process.

In recent years, the development and usage of focused ion beam (FIB) microscopes have become increasingly popular. By utilizing an ion beam as the emitting source, the FIB microscope is able to perform various analyses or circuit edits on different materials. The structure of a standard FIB microscope is nevertheless complex, including components such as liquid metal ion source (LMIS), electro-lens, scanning electrodes, secondary particle detector, specimen base capable of axial movements, vacuum system, and anti-vibration and anti-magnetic field devices. In general, when an electric field is applied to a liquid metal ion source such as liquid gallium (Ga), the liquid gallium is transformed into a shape with a tiny pointy tip, and by utilizing a negative electric field, the gallium ion can be extracted from the pointy tip.

After being focused by the electro-lens and a series of aperture size alterations, the size of the ion source is confirmed, and after passing the ion beam to the surface of the specimen via a second focusing, the ion beam is able to perform operations including incision and drilling. Having numerous advantages including a low melting point, a low vaporizing pressure, and strong anti-oxidizing capability, gallium has been a popular liquid metal ion source in various commercial systems. Moreover, due to the development of FIB microscopes, semiconductor industries are able to fabricate precise scanning electron microscope (SEM) cross-sectional specimens or transmission electron microscope (TEM) cross-sectional specimens to perform micro-area analyses.

In addition to the fabrication of cross-section specimens provided by transmission electron microscopes, the FIB microscopes provide an alternative specimen fabrication tool for the users, in that the FIB microscopes are capable of achieving a success rate of greater than 90% within a working hour between 2–6 hours, and by utilizing the specimens fabricated by the FIB microscopes, the transmission electron microscopes are able to obtain satisfactory resolution and contrast results. However, when the ions collide with the specimens, phenomena such as gasification and ionization will occur on the surface of the specimen, neutral atoms, ions, and electrons will be produced, and a small quantity of the ions will be implanted into the specimen. The implanted ions are all destructive in nature and when these focused ion beams are utilized to fabricate cross-sectional specimens from a defect located on the surface of a wafer, the defect or the surface of the wafer will be damaged. In mild cases, an amorphous layer containing the ion source element (gallium in general) will form over the surface of the specimen, whereas in severe cases, precipitate containing the ion source element will be generated. At any rate, either case will damage the specimen and influence the result of the observation. When the defect is not located on the surface layer of the specimen, a layer disposed on the defect will be first removed to expose the defect. Next, a scanning electron microscope or an optical microscope is used to perform a top-view observation on the defect and a focused ion beam is used to fabricate a cross-sectional specimen. In either condition, the chance of damaging the defect remains the same.

Recently, a new type of FIB microscope referred to as the dual beam system has been introduced. Capable of providing two particle beams (ion beam plus electron beam) simultaneously, the electron beam of the dual beam system can be utilized to form a platinum (Pt) protective layer over the surface of the defect. Despite having several advantages, the dual beam system still remains unpopular as a result of an overly high cost and other problems caused during fabrication of cross-section specimens. Please refer to FIG. 1. FIG. 1 is a perspective diagram showing the method of fabricating a TEM cross-section specimen 10 by using a FIB microscope of a dual beam system according to the prior art. (As shown in FIG. 1, the TEM cross-section specimen 10 comprises a plurality of trenches 12 thereon and when the trenches 12 are not filled with stuffing materials, the platinum layer formed by evaporation process will not only cover a defect 14, but also will fill the trenches 12 (both not shown in the figure). Since the high atomic number and electron scattering of the platinum layer is much stronger, the electrons are not likely to penetrate the layer and black areas will be produced as a result of contrast difference, thereby blocking the defect 14 and increasing the difficulty of observation.

Additionally, a conventional method of utilizing transparent resin or glue to cover the specimen entirely has also been introduced. Despite the fact that this method is effective for increasing the contrast between the protective layer and the surface layer structure, it is unfortunately ineffective for searching and confirming the exact location of the defect by utilizing the FIB microscope. Because the electrical conductivity of the protective layer produced by the method is poor, thereby resulting in electron charging. As the electron charging occurs, the precise location of the defect will be difficult to determine.

Hence it remains a challenge to provide a default analysis method that is not only able to provide a protective layer for the defect while the focused ion beam is utilized for fabricating a specimen, but that can also accurately determine the location of the defect and perform necessary observations by preventing the blocking of the defect and the electron charging.

SUMMARY OF INVENTION

It is therefore an objective of the present invention to provide a method of defect analysis by applying a nondestructive micro-protection for solving the above-mentioned problems.

According to the present invention, a method of defect analysis by applying at least one micro-protection comprises: providing a substrate, in which the substrate includes at least a defect thereon; forming a micro-protection on the surface of the defect; confirming the site of the defect; and utilizing a focused ion beam (FIB) microscope for forming a specimen of the defect.

In contrast to the conventional method, the present invention provides a defect analysis method by creating at least a reference mark in proximity to the defect, performing a layer removing process for exposing the layer where the defect is located or performing the layer removing process before the reference mark is created, and forming a non-destructive micro-protection on the defect. Alternatively, the reference mark can be created after the formation of the non-destructive micro-protection. Hence, the method is not only able to confirm the location of the defect by utilizing the FIB microscope to search the reference mark in proximity to the defect, but also to utilize the partial coverage of the micro-protection to protect the defect from any damage when the focused ion beam continuously scans the substrate. Since the micro-protection only partially covers the defect, problems such electron charging can be effectively prevented. Additionally, a scanning electron microscope can be utilized to observe the top-view structure of the defect, and after the transmission electron microscope specimen of the defect is fabricated by the FIB microscope, a transmission electron microscope can be utilized to analyze the cross-sectional structure of the defect while performing the defect analysis. By utilizing this method, the same defect can be analyzed simultaneously by both top-view analysis and cross-sectional analysis without additional sampling, thereby increasing the accuracy of determining the root cause of the defect and reducing the amount of analytical time and sampling risk.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
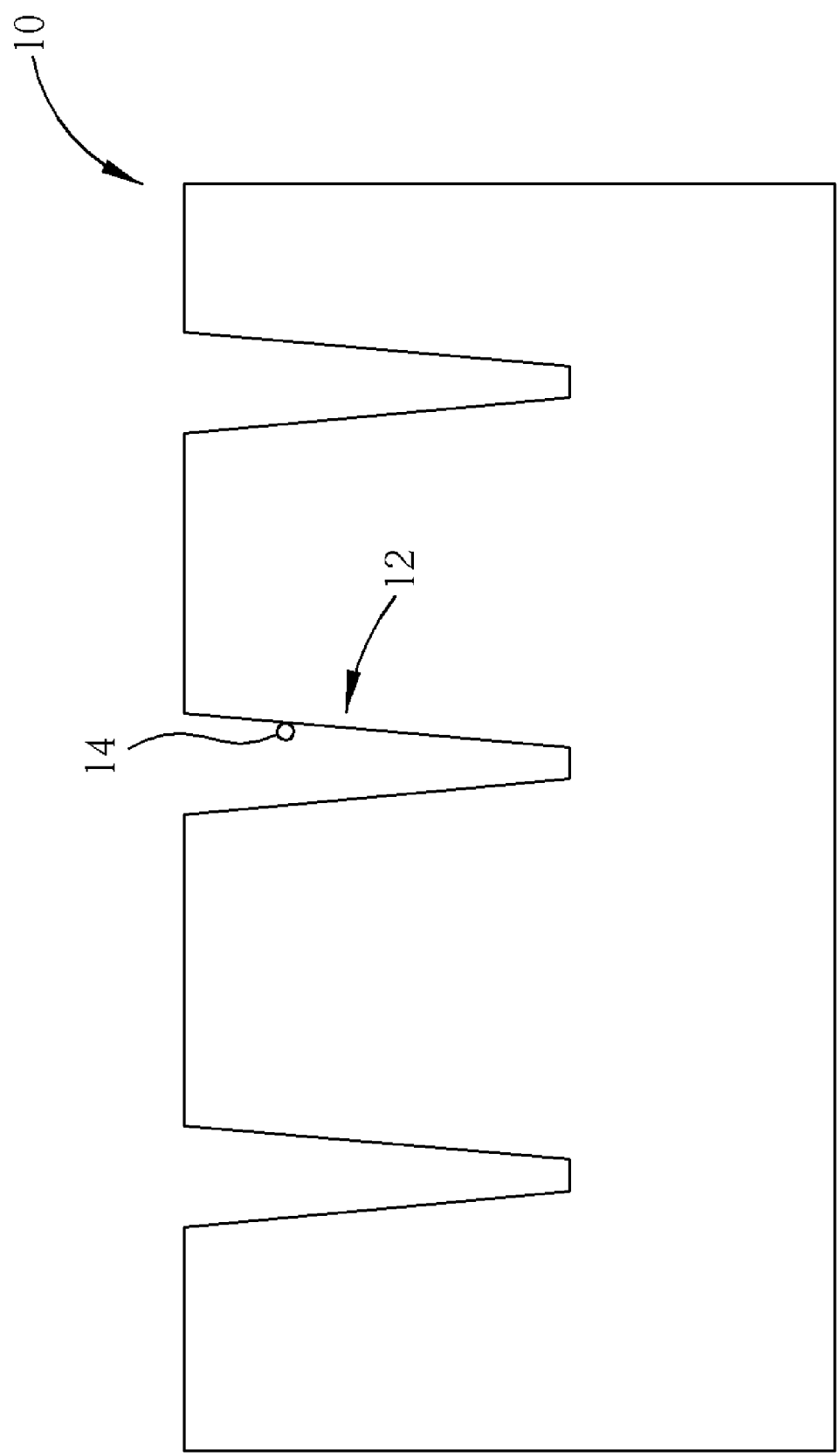
FIG. 1 is a perspective diagram showing the method of fabricating a transmission electron microscope cross-section specimen by using a focused ion beam microscope of a dual beam system according to the prior art.
Figure 2:
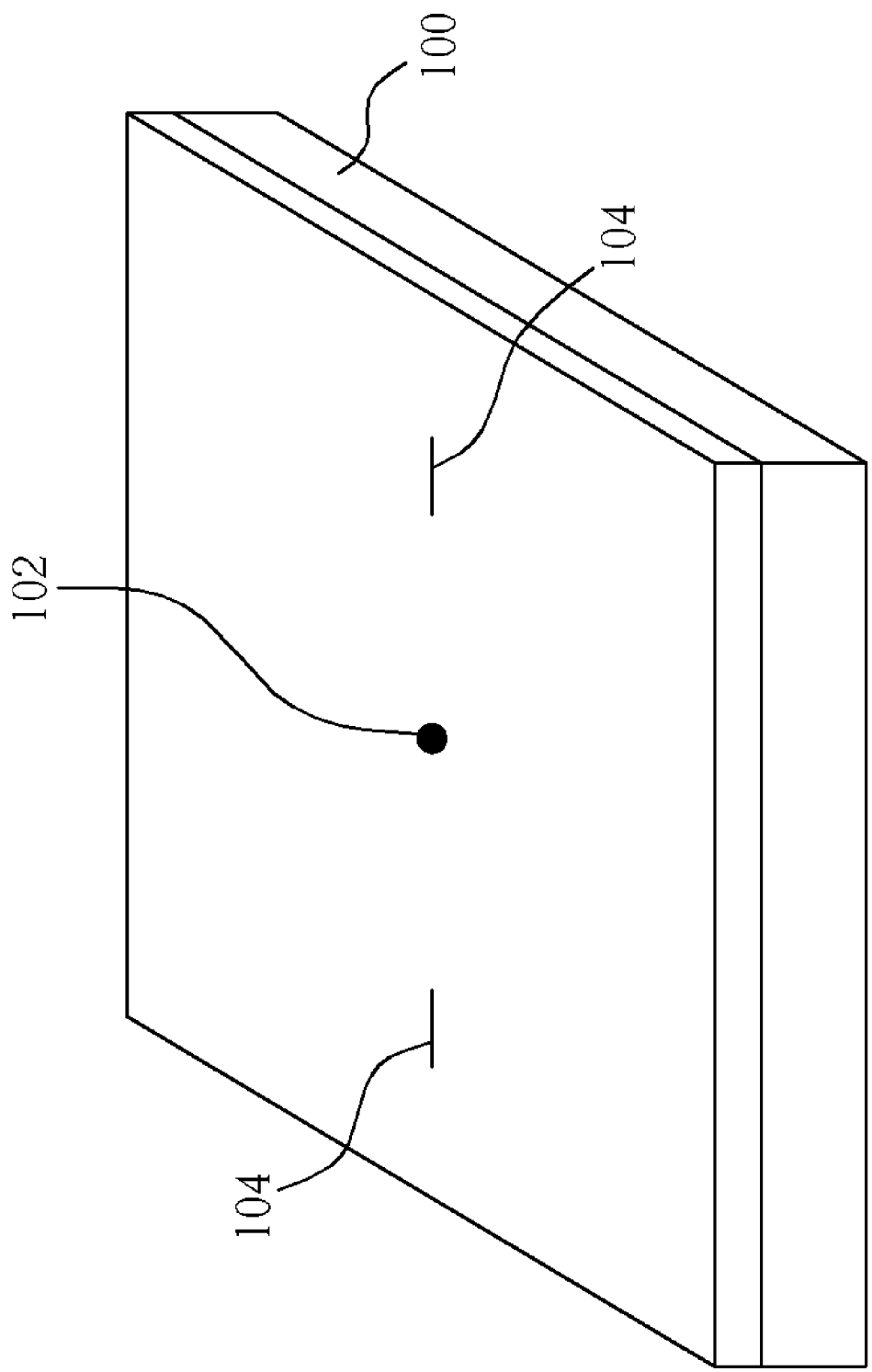
FIG. 2 through FIG. 6 are perspective diagrams showing the defect analysis by applying the micro-protection according to the present invention.
Figure 5:
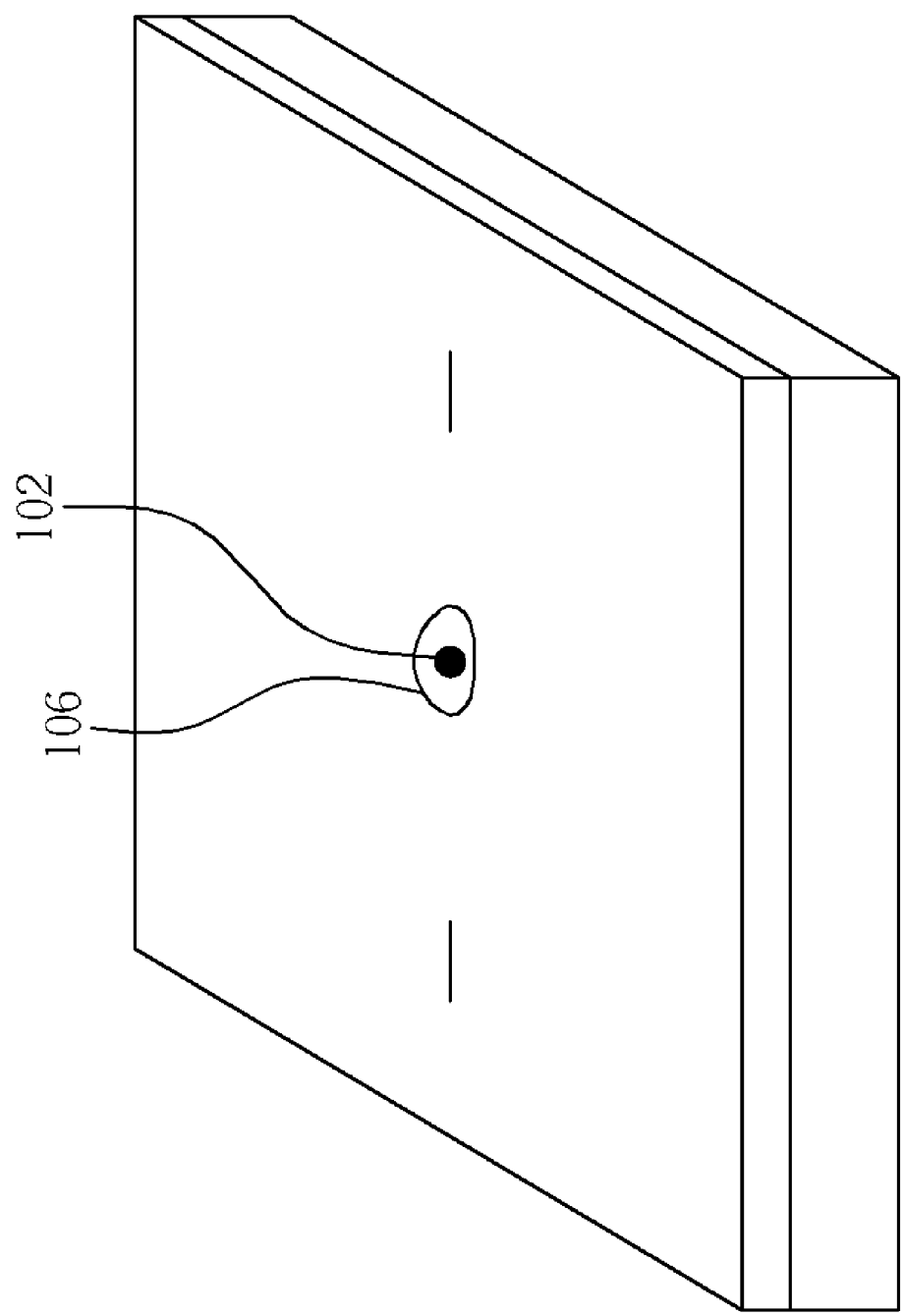
Figure 6:
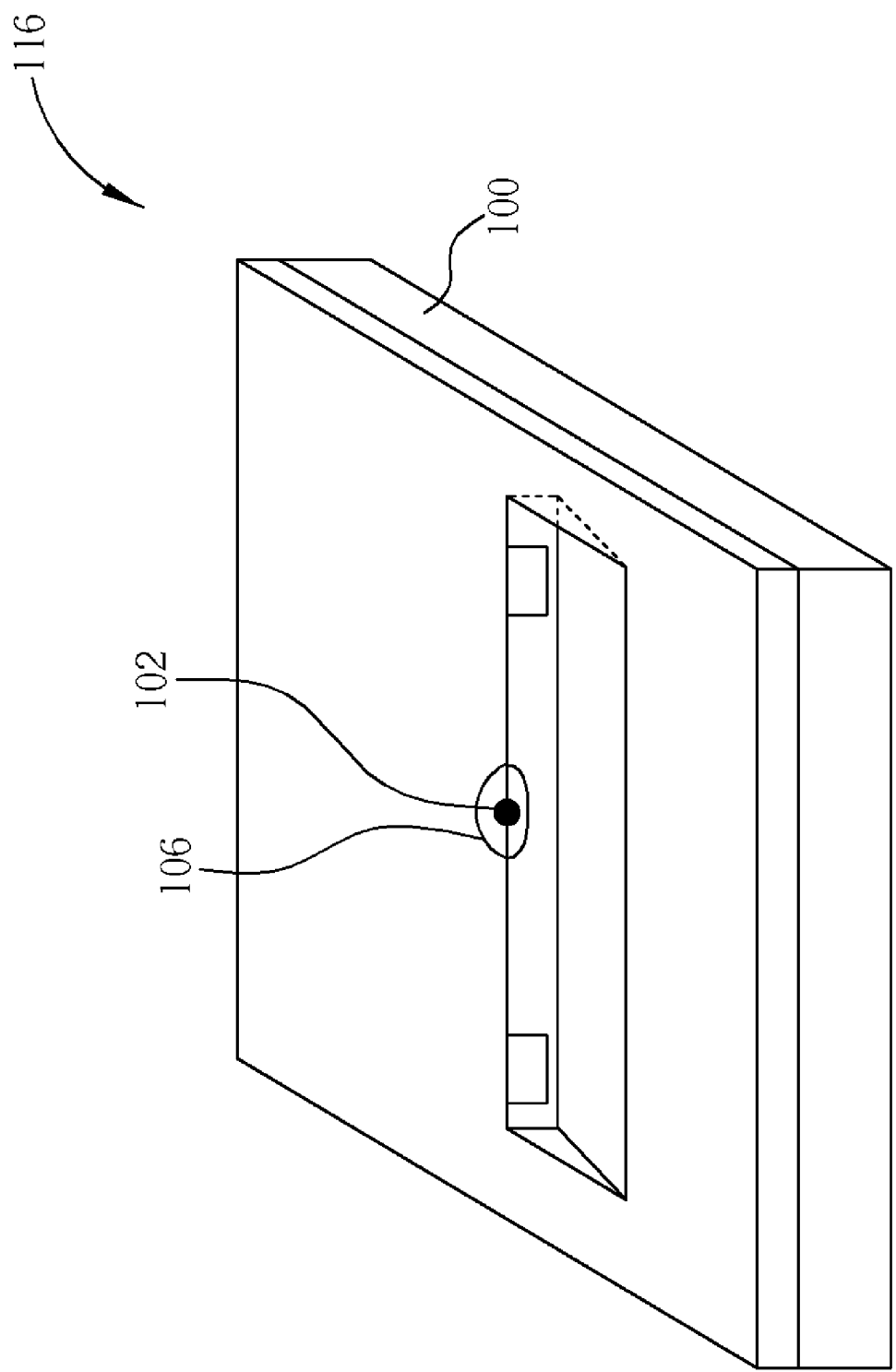
Figure 7:
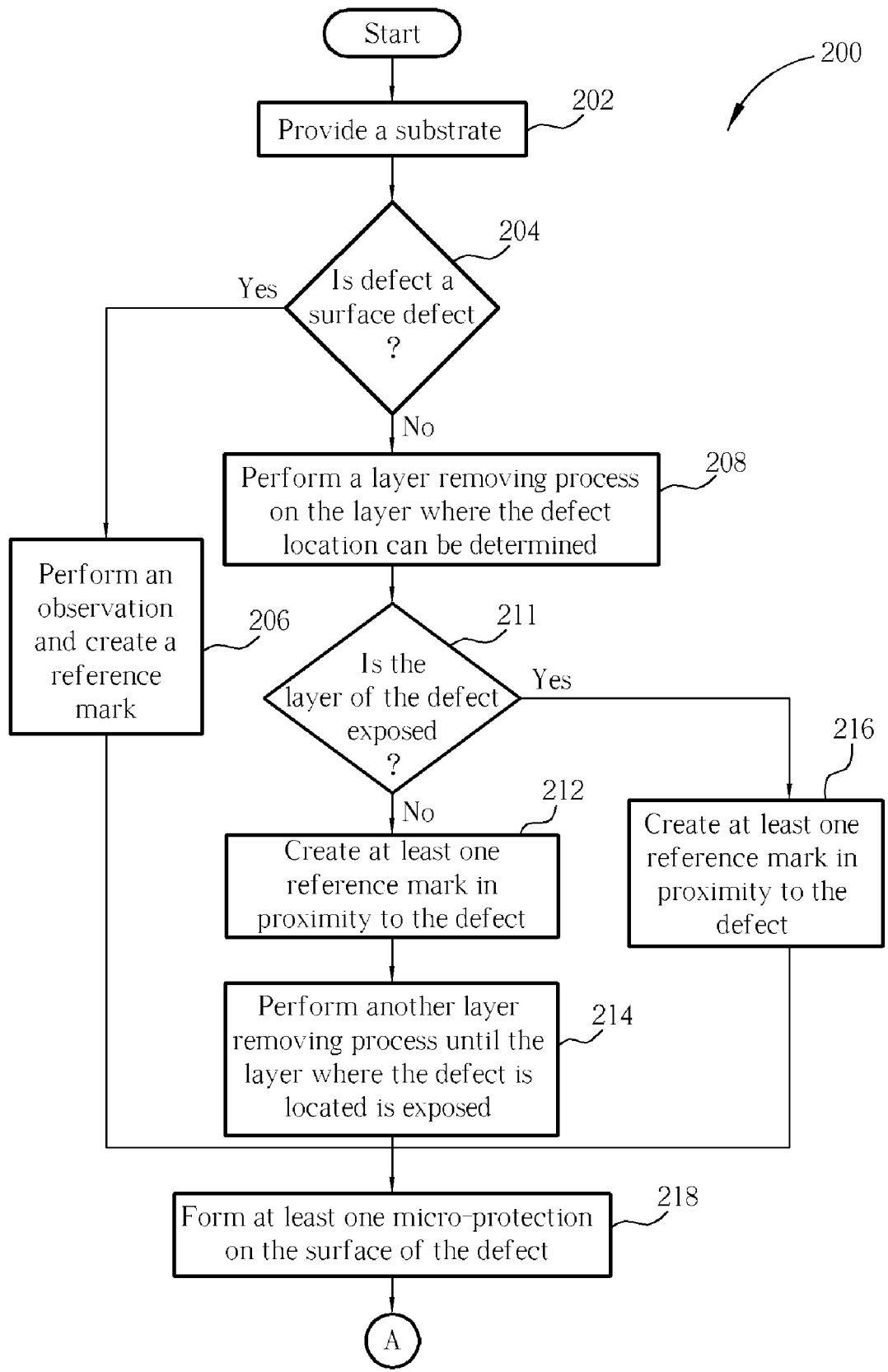
FIG. 7 through FIG. 8 are flowchart diagrams showing the defect analysis by applying the micro-protection according to the present invention.
Figure 8:
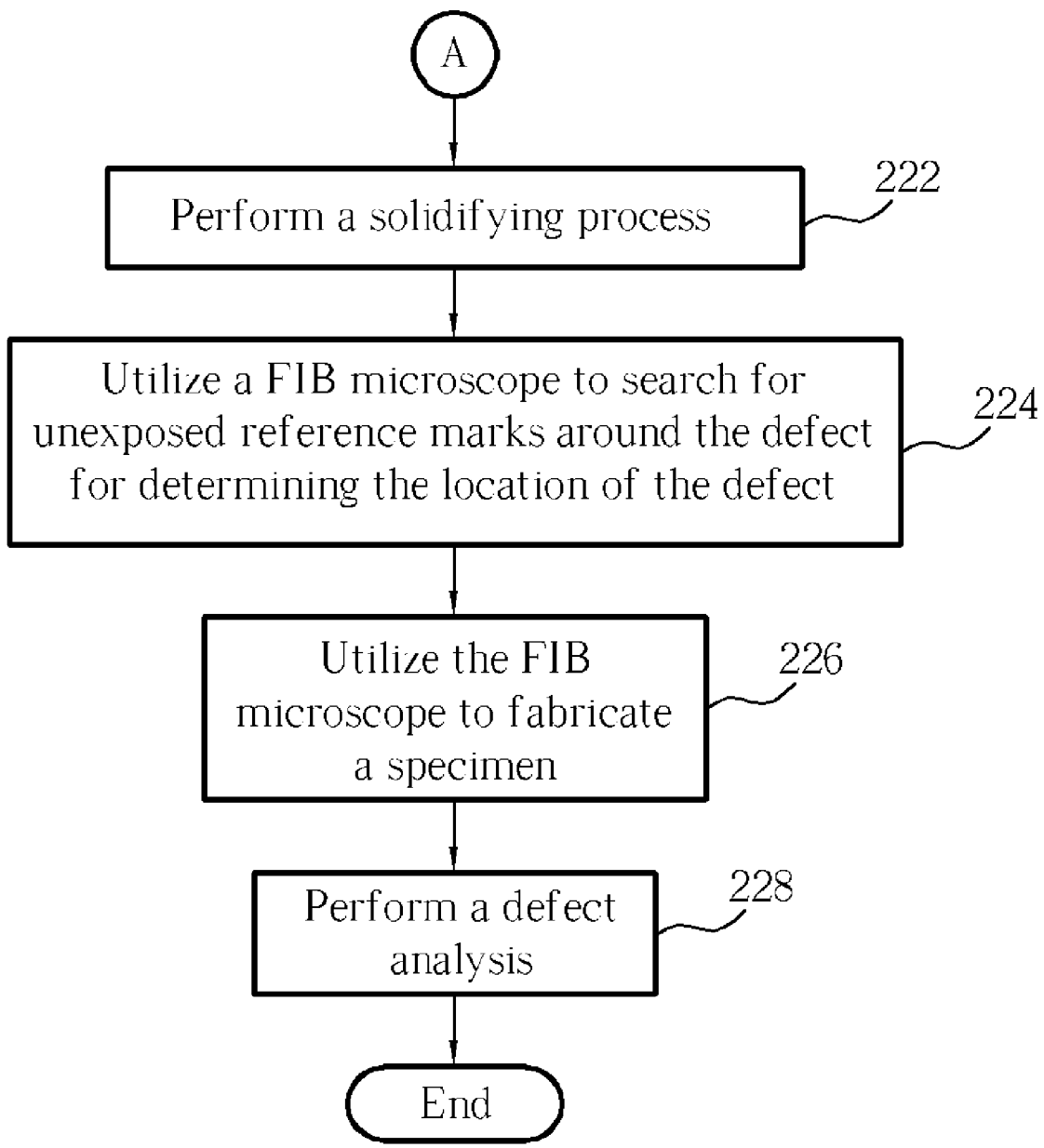

Please refer to FIG. 2 through FIG. 8. FIG. 2 through FIG. 6 are perspective diagrams showing the defect analysis by applying the micro-protection according to the present invention, and FIG. 7 through FIG. 8 are flowchart diagrams showing the defect analysis by applying the micro-protection. As shown in FIG. 2 and FIG. 7, a substrate 100 is first provided according to step 202, in which the substrate 100 can be a wafer or a glass substrate. The substrate 100 includes a defect 102 thereon, in which the defect 102 can be a surface defect or a bottom layer defect. Next, whether the defect is a surface defect is determined according to step 204. If the defect 102 is a surface defect (as shown in FIG. 2), an observation is performed to observe the substrate 100 by utilizing a microscope, and at least a reference mark 104 is created (step 206) in proximity to the defect 102. The reference mark can be a feature of a surface structure or a laser mark, and the microscope can be an optical microscope or a scanning electron microscope.

Figure 3:
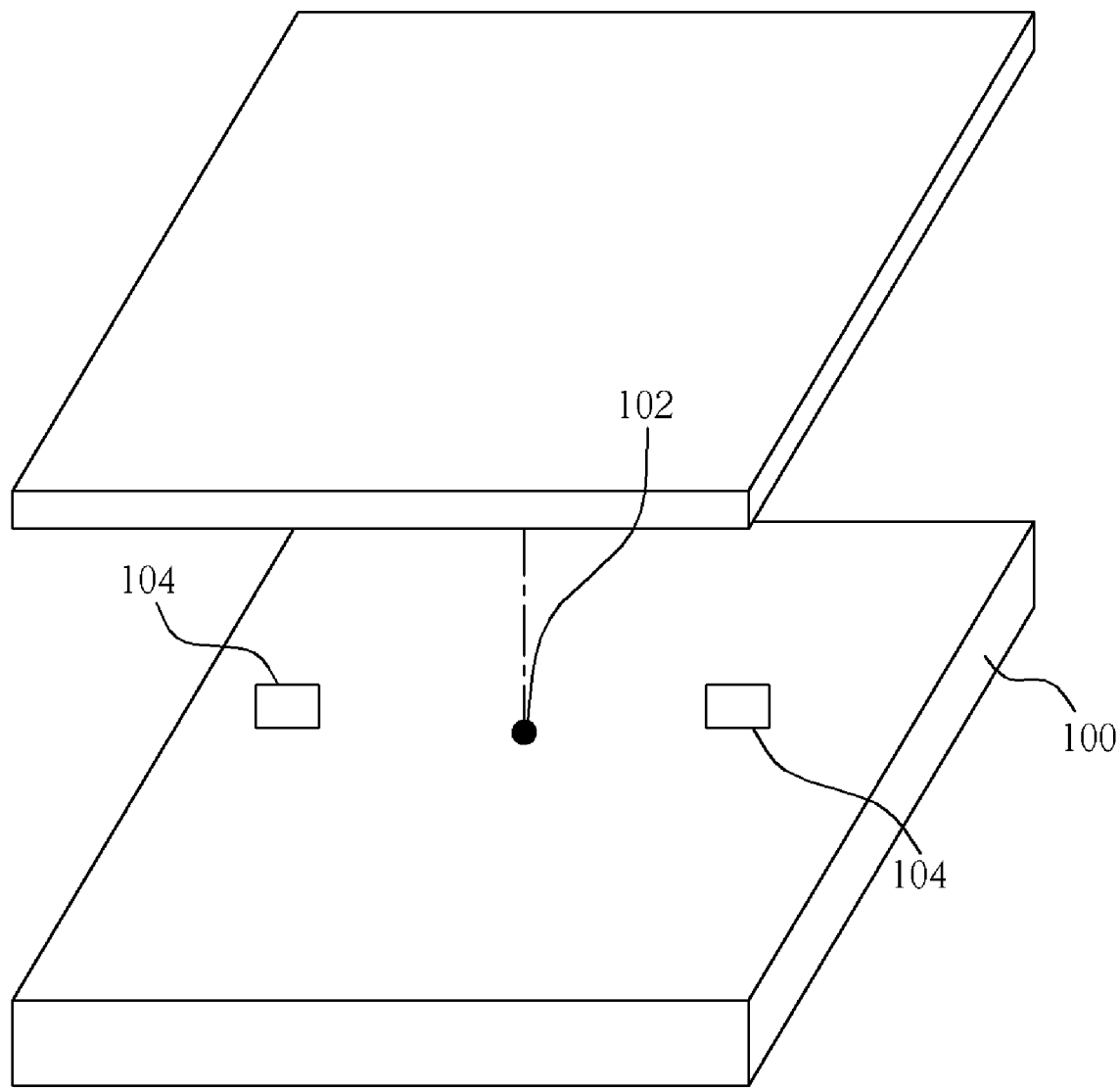

Alternatively, the defect 102 can also be a bottom layer defect, such as the defect 102 shown in FIG. 3. When the defect 102 is a bottom layer defect, as shown in FIG. 3 and FIG. 7, a layer removing process (step 208) is performed to remove the material layer formed on the substrate 100 layer after layer, in which the layer removing process can be carried out physically (via plasma etching) or chemically (via solution reactions). When the layers are being removed, an optical microscope or a scanning electron microscope is utilized to observe the surface of the substrate 100 to ensure that the defect is not damaged and at least a reference mark 104 is created in proximity to the defect according to step 212. Next, another layer removing process is performed to expose the layer containing the defect, according to step 214. Similarly, the reference mark 104 includes a feature located on a bottom layer structure, a focused ion beam mark, or a laser mark. Since the depth of the reference mark 104 fabricated by the laser or focused ion beam is usually much deeper, the reference mark 104 has to be created before the layers are removed, thereby preventing damage to the defect 102 and ensuring that the reference mark 104 is clearly visible.

When the defect 102 is a bottom layer defect, sometimes the location of the defect can be determined by partially removing the layer on top of the defect. After the location of the defect is confirmed, reference marks can then be created according to step 212. Under different situations, the layer on top of the defect may have to be removed completely to determine the location of the defect before creating any reference mark (step 216). Since the defect is already exposed, the reference mark 104 is usually created by utilizing a specific feature on the layer structure or by a laser under an optical microscope to prevent damage to the defect 102.

Figure 4:
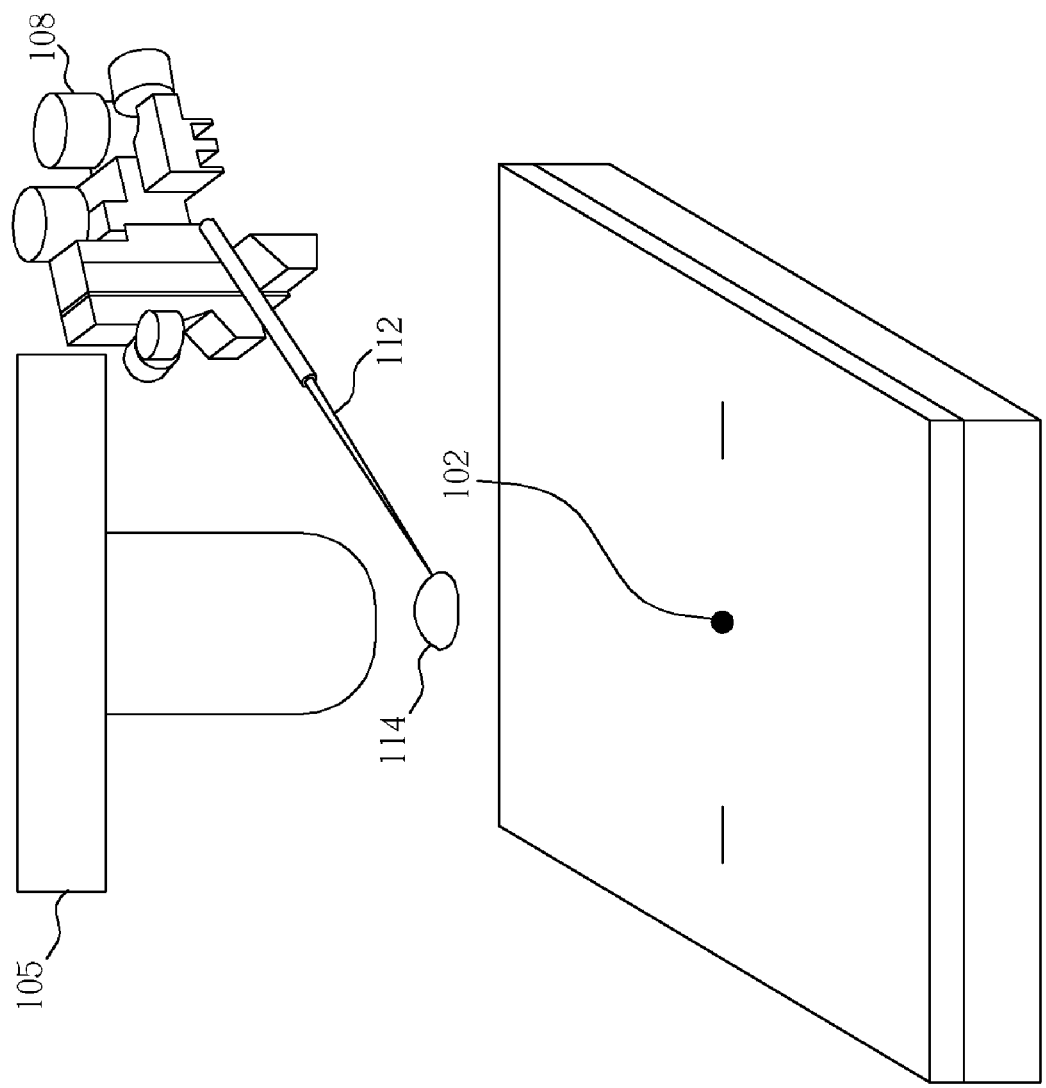

Next, at least a micro-protection is formed on the surface of the defect according to step 218. As shown in FIG. 4 and FIG. 7, the method of fabricating a micro-protection 106 first includes placing a small quantity of transparent material 114 on the surface of the defect 102 by utilizing a probe 112, which is controlled by a micromanipulator 108 under an optical microscope 105. Next, a solidifying process (step 222) is performed to solidify the transparent material 114 for forming a micro-protection 106 on the surface of the defect 102, as shown in FIG. 5 and FIG. 8. Preferably, the transparent material 114 is comprised of transparent resin or glue, and the solidifying process can be heating or at room temperature.

As shown in FIG. 8, a focused ion beam microscope is then utilized to find any other unexposed reference marks around the defect (step 224). In order to search for the unexposed reference marks, the substrate 100 is placed under a focused ion beam microscope to locate any visible reference mark 104 and the reference marks 104 are then used to determine the location of the defect 102. By covering the defect 102 partially, the micro-protection 106 is able to serve as a protective layer to the defect 102 for preventing damage and electron charging when the focused ion beam continuously scans the substrate 100. Furthermore, transparent materials are usually organic compounds and composed of low atomic number elements (ex. C, H, and O). Since the electron scattering of low atomic number elements is weak, the electrons can easily pass through them without scattering. The transparent materials will not block the defect when using TEM to observe. Preferably, the micro-protection 106 is comprised of non-destructive materials including transparent resin or glue.

Next, a specimen is fabricated by using the focused ion beam microscope (step 226), as shown in FIG. 6 and FIG. 8. According to step 226, a specimen 116 of the defect 102 is produced by utilizing the focused ion beam of the FIB microscope to cut a cross-section from the substrate 100, in which the specimen 116 can be a scanning electron microscope specimen or further cut to a transmission electron microscope specimen. Similarly, by covering the defect 102 partially, the micro-protection 106 is able to serve as a protective layer to the defect 102 for preventing damage and electron charging when the focused ion beam is utilized for cutting the substrate 100. Next, a defect analysis (step 228) is performed to examine the specimen 116 fabricated from step 226 by inserting the specimen 116 into a scanning electron microscope. Preferably, the scanning electron microscope can be utilized for examining the cross-sectional structure of the defect 102 or the structure of the defect at an angle (one of the functions of the scanning electron microscope being to tilt a specimen at an observable angle).

Additionally, a scanning electron microscope can be utilized selectively for observing the top-view structure of the defect 102 after step 206, 214, and 216 and before step 218. Next, a transmission electron microscope specimen can be produced when a specimen of the defect is fabricated by the FIB microscope (step 226), and a transmission electron microscope can be utilized to perform the defect analysis (step 228) for analyzing the cross-sectional structure of the defect 102. Since the micro-protection 106 is not yet fabricated when the top-view structure of the defect 102 is observed by the scanning electron microscope, problems such as electron charging are not likely to occur and at the same time, the same specimen 116 can be utilized for both top-view analysis and cross-sectional analysis without using additional specimens. In other words, the present invention is able to observe the defect on the specimen 116 by utilizing both the top-view analysis and the cross-sectional analysis, thereby acquiring much more information regarding to the defect, increasing the accuracy for determining the cause of the defect, and reducing the risk of sampling error. By utilizing the same specimen for both analyses instead of utilizing one specimen for the top-view analysis and another specimen for the cross-sectional analysis, the present invention is able to provide better results when the defect cause of each specimen is different.

Figure 9:
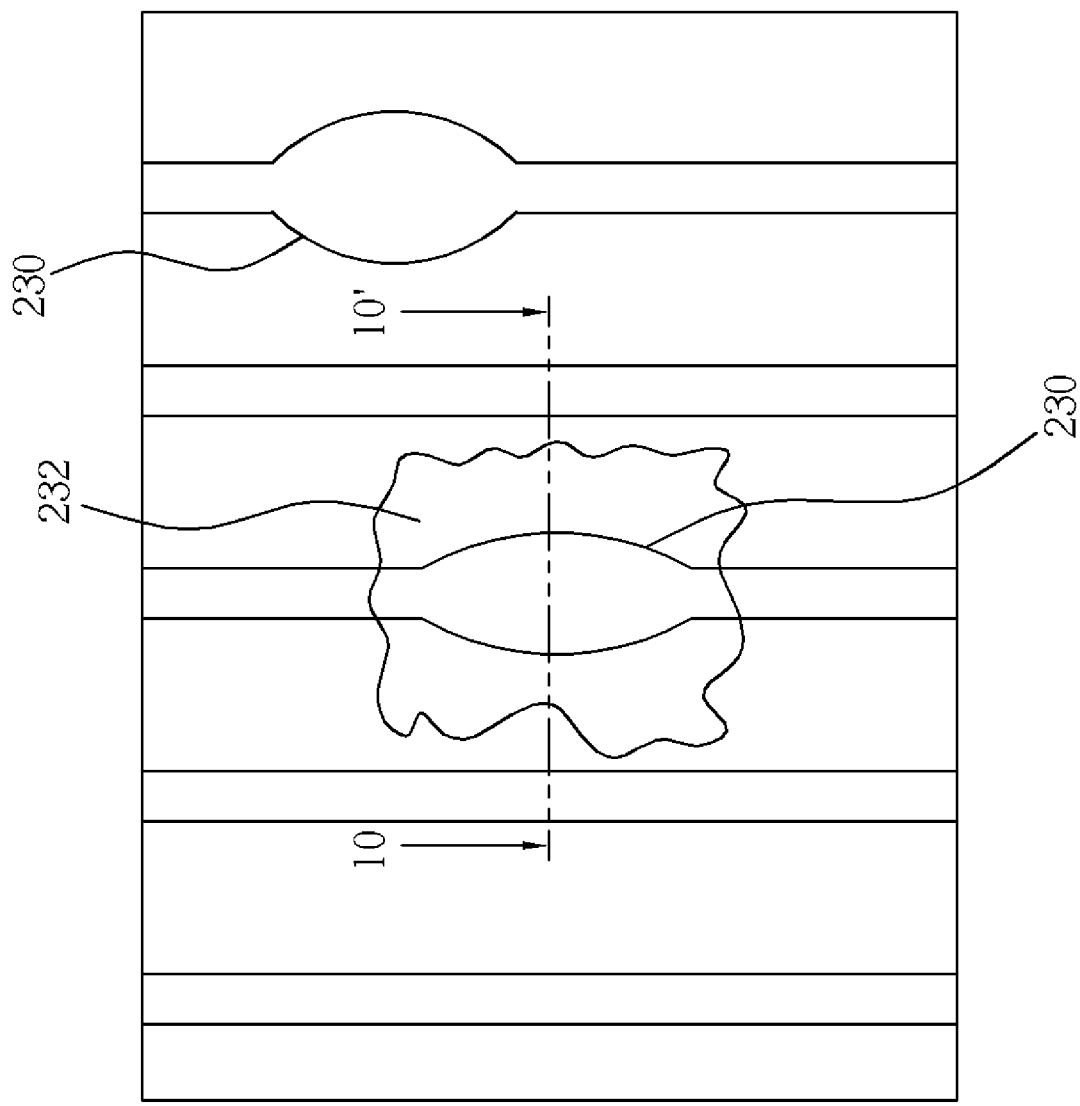
FIG. 9 is a perspective diagram showing the top-view of the defect of the contact hole observed by a scanning electron microscope according to the present invention.
Figure 10:
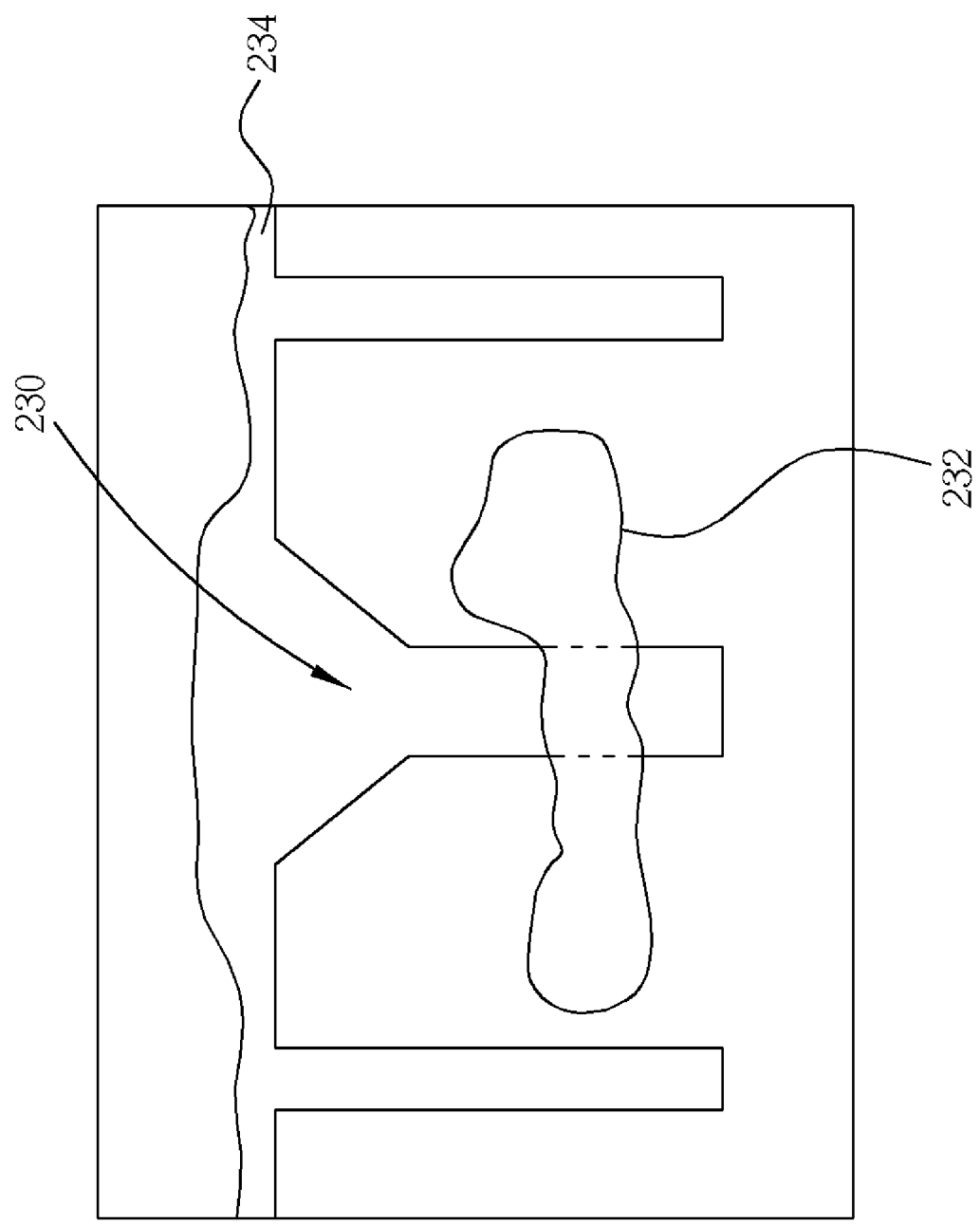
FIG. 10 is a perspective diagram showing the cross-section of the defect of the contact hole observed by a transmission electron microscope along line 10–10' of FIG. 9 according to the present invention.

Please refer to FIG. 9 and FIG. 10. FIG. 9 is a perspective diagram showing the top view of a defect 232 of the contact hole 230 observed by a scanning electron microscope according to the present invention whereas FIG. 10 is a perspective diagram showing the cross-section of the defect 232 of the contact hole 230 observed by a transmission electron microscope along line 10–10' of FIG. 9. As shown in FIG. 9, the defect 232 is included within the central contact hole 230 (please refer to the normal contact hole on the right). After the top-view structure information regarding to the defect 232 is collected by the scanning electron microscope, steps including formation of at least one micro-protection (step 218), solidifying process (step 222), and utilizing an FIB microscope to search for uncovered reference marks in proximity to the defect for determining the site of the defect (step 226) are performed over the surface of the defect. Next, a transmission electron microscope specimen along a sectional line 10–10' of FIG. 9 is fabricated when an FIB microscope is utilized for creating a specimen (step 226). After the transmission electron microscope specimen is obtained, a defect analysis is performed (step 228) by utilizing a transmission electron microscope to observe the defect 232 of the contact hole 230 for producing the result as shown in FIG. 10. As shown in FIG. 10, the specimen has been cut accurately and the defect 232 has remained undamaged due to the protection of the micro-protection 234.

Figure 11:
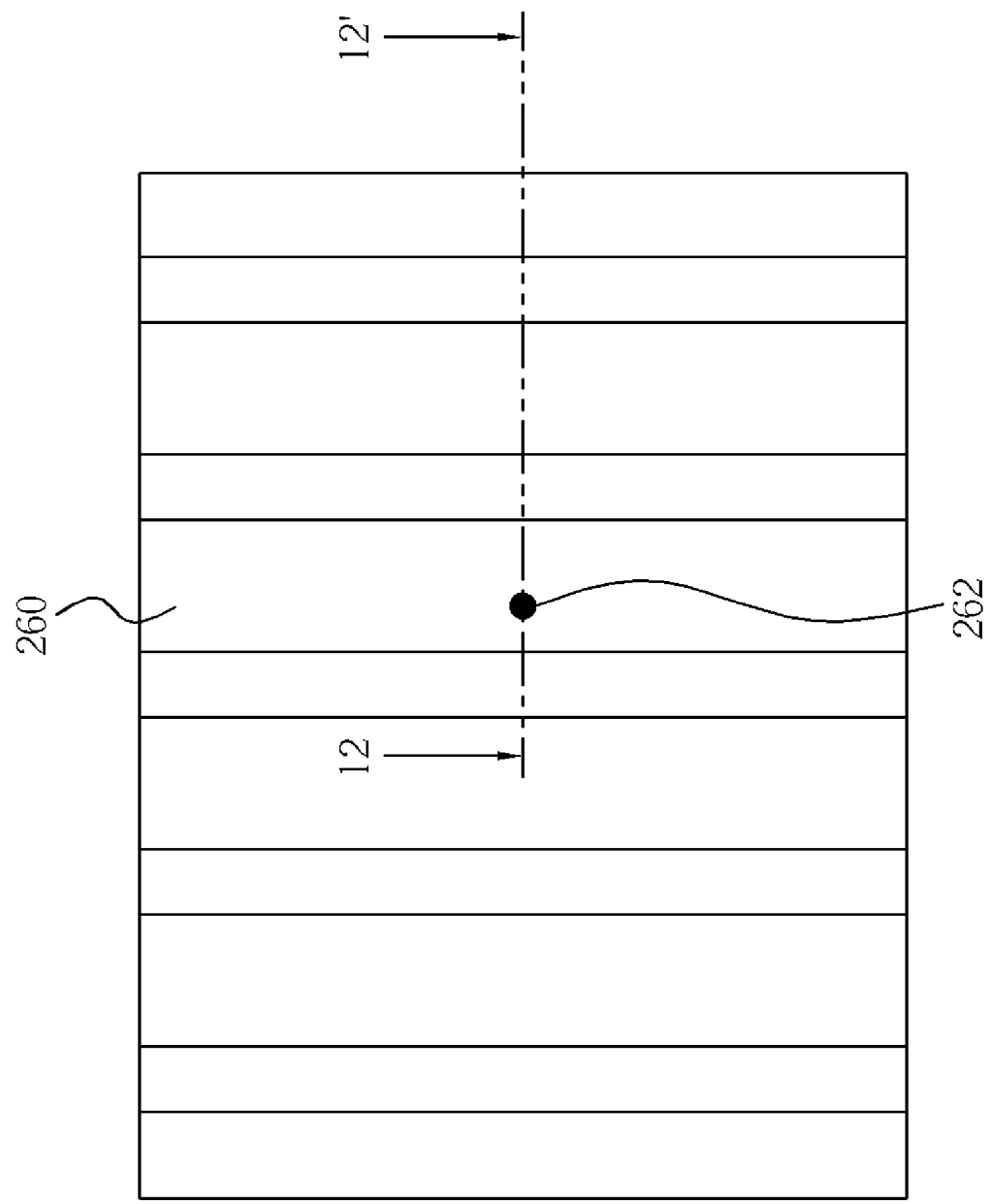
FIG. 11 is a perspective diagram showing the top-view of a word line defect observed by a scanning electron microscope according to the present invention.
Figure 12:
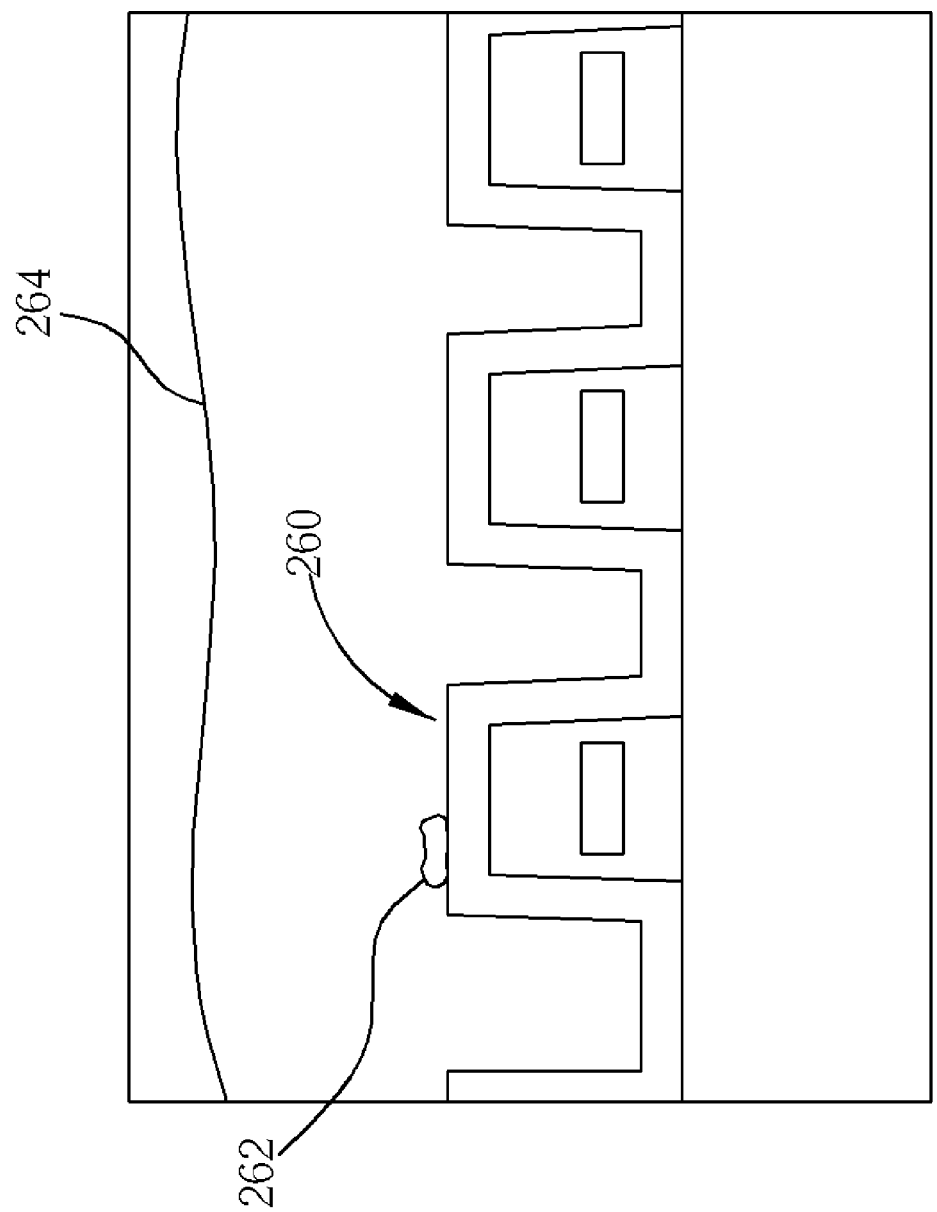
FIG. 12 is a perspective diagram showing the cross-section of the word line defect observed by a transmission electron microscope along line 12–12' of FIG. 11 according to the present invention.

Please refer to FIG. 11 and FIG. 12. FIG. 11 is a perspective diagram showing the top-view structure of the defect 262 of a word line 260 observed by a scanning electron microscope according to the present invention whereas FIG. 12 is a perspective diagram showing the cross-section of the defect 262 of the word line 260 observed by a transmission electron microscope along a sectional line 12–12' of FIG. 11. As shown in FIG. 11, the defect 262 is included on the word line 260 (please refer to other normal word lines). After the top-view structure information regarding to the defect 262 is collected by the scanning electron microscope, steps including formation of at least one micro-protection (step 218), a solidification process (step 222), and utilizing an FIB microscope to search for uncovered reference marks in proximity to the defect for determining the site of the defect (step 226) are performed over the surface of the defect. Next, a transmission electron microscope specimen along a sectional line 12–12' of FIG. 11 is fabricated when an FIB microscope is utilized for creating a specimen (step 226). After the transmission electron microscope specimen is obtained, a defect analysis is performed (step 228) by utilizing a transmission electron microscope to observe the defect 262 of the word line 260 for producing the result as shown in FIG. 12. As shown in FIG. 12, the specimen has been cut accurately and the defect 262 has remained undamaged due to the protection of the micro-protection 264.

According to the method disclosed by the present invention, at least a reference mark is created in proximity to the defect and a layer removing process is performed for exposing the layer where the defect is situated. Alternatively, a layer removing process can be performed before the reference mark is created on the same layer as the defect and finally, a non-destructive micro-protection is then formed on top of the defect. Hence, the location of the defect can be accurately confirmed and by utilizing the partial coverage of the micro-protection, the defect can be well protected from any damage caused by the focused ion beam. At the same time, problems caused during observations or the electron charging can also be greatly reduced. Consequently, when the present method is applied to an actual production line, various specimens containing defects can be created successfully and information regarding each defect can be easily extracted. Moreover, different analyses can be applied to a same defect, thereby increasing the accuracy of determining the cause of the defect and reducing the amount of determination time.

In contrast to the conventional method, the present invention provides a defect analysis method by creating at least a reference mark in proximity to the defect, performing a layer removing process for exposing the layer where the defect is located or performing the layer removing process before the reference mark is created, and forming a non-destructive micro-protection on the defect. Alternatively, the reference mark can be created after the formation of the non-destructive micro-protection when the size of the defect is greater than a critical size (the critical size will be based on the specification of the product, the experience level, and the limit of the fabrication process). By doing so, the method is not only able to confirm the location of the defect by utilizing the FIB microscope to search the reference mark in proximity to the defect, but is also able to utilize the partial coverage of the micro-protection to protect the defect from any damage when the focused ion beam is continuously fired on the substrate. Since the micro-protection only partially covers the defect, problems such as the electron charging can be effectively prevented. Additionally, a scanning electron microscope can be utilized to observe the top-view structure of the defect, and after the transmission electron microscope specimen of the defect is fabricated by the FIB microscope, a transmission electron microscope can be utilized to analyze the cross-sectional structure of the defect while performing the defect analysis. By utilizing this method, the same defect can be analyzed simultaneously by both top-view analysis and cross-sectional analysis without additional sampling, thereby increasing the accuracy of determining the root cause of the defect and at the same time reducing the amount of analytical time and sampling risk.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A method of defect analysis comprising:
    providing a substrate, the substrate includes at least a defect thereon;
    utilizing at least one microscope for observing the substrate;
    creating a reference mark in proximity to the defect;
    forming a micro-protection on the surface of the defect;
    confirming the site of the defect; and
    utilizing a focused ion beam (FIB) microscope to form a specimen of the defect.

2. The method of claim 1, wherein the substrate is a wafer or a glass substrate.

3. The method of claim 1, wherein the defect is a surface defect.

4. The method of claim 1, wherein the microscope is an optical microscope or a scanning electron microscope (SEM), and the specimen is a transmission electron microscope (TEM) specimen or a scanning electron microscope specimen.

5. The method of claim 1 further comprising performing a layer removing step to expose the defect after the reference mark is created.

6. The method of claim 1 further comprising performing a layer removing step to expose the defect before the reference mark is created.

7. The method of claim 1 further comprising determining the location of the reference mark when the site of the defect is confirmed by the focused ion beam microscope, wherein the reference mark comprises a feature, a focused ion beam mark, or a laser mark.

8. The method of claim 1 further comprising utilizing a scanning electron microscope for observing the top-view structure of the defect before the micro-protection is formed on the surface of the defect.

9. The method of claim 1, wherein the step of forming a micro-protection on the surface of the defect further comprises:
    placing a small quantity of transparent material on the surface of the defect; and
    solidifying the disposed transparent material.

10. The method of claim 9, wherein the step of placing the small quantity of transparent material on the surface of the defect is performed by using an optical microscope and a probe of a micromanipulator.

11. The method of claim 9, wherein the transparent material comprises transparent resin or glue.

12. A method of defect analysis comprising:
    providing a substrate, wherein the substrate includes at least a defect thereon;
    creating at least one reference mark in proximity to the defect;
    forming a micro-protection on the surface of the defect;
    utilizing a focused ion beam (FIB) microscope to search the reference mark for confirming the site of the defect; and
    forming a specimen of the defect by utilizing the focused ion beam microscope.

13. The method of claim 12, wherein the substrate is a wafer or a glass substrate, the defect is a surface defect or a bottom layer defect, and the reference mark comprises a feature, a focused ion beam mark, or a laser mark.

14. The method of claim 12 further comprising a layer removing step when the defect is a bottom layer defect and after the reference mark is created.

15. The method of claim 12 further comprising a layer removing step when the defect is a bottom layer defect and before the reference mark is created.

16. The method of claim 12, wherein the step of forming a micro-protection on the surface of the defect further comprises:
    placing a small quantity of transparent material on the surface of the defect; and
    solidifying the disposed transparent material.

17. The method of claim 16, wherein the step of placing the small quantity of transparent material on the surface of the defect is performed by using an optical microscope and a probe of a micromanipulator.

18. The method of claim 16, wherein the transparent material comprises transparent resin or glue.

19. The method of claim 12, wherein the specimen is a transmission electron microscope specimen or a scanning electron microscope specimen.

* * * * *